United States Patent [19]

Jautelat et al.

[11] Patent Number: 5,760,067
[45] Date of Patent: Jun. 2, 1998

[54] HALOGEN ALKENYL AZOLYL MICROBICIDES

[75] Inventors: Manfred Jautelat, Leverkusen; Stefan Dutzmann, Hilden; Heinz-Wilhelm Dehne, Bonn, all of Germany

[73] Assignee: Bayer Aktiengesellschaft, Leverkusen, Germany

[21] Appl. No.: 676,304

[22] Filed: Jul. 18, 1996

[30] Foreign Application Priority Data

Jan. 25, 1994 [DE] Germany .................. 44 02 034.1

[51] Int. Cl.$^6$ .................. A01N 43/653; C07D 249/08
[52] U.S. Cl. .................. 514/383; 514/184; 548/101; 548/267.2; 548/267.4; 548/217.8; 548/268.6
[58] Field of Search .................. 548/101, 267.2, 548/267.4, 267.8, 268.6; 514/184, 383

[56] References Cited

U.S. PATENT DOCUMENTS

| | | | |
|---|---|---|---|
| 4,655,820 | 4/1987 | Worthington et al. | 71/92 |
| 5,122,532 | 6/1992 | Jautelat et al. | 514/383 |
| 5,143,932 | 9/1992 | Jautelat et al. | 514/383 |

OTHER PUBLICATIONS

Cram & Hammond, "Organic Chemistry", McGraw–Hill Book Co NY, 2nd Ed. pp. 565–567, 1964.

*Primary Examiner*—Patricia L. Morris
*Attorney, Agent, or Firm*—Sprung Kramer Schaefer & Briscoe

[57] ABSTRACT

Novel halogenoalkenyl-azolyl derivatives of the formula $$R^1-\underset{\underset{\underset{\underset{N}{\overset{\|}{\underset{N}{\diagdown}}}}{\overset{|}{CH_2}}}{\overset{|}{C}}}{\overset{OH}{|}}-CH_2-\overset{X^1}{\overset{|}{C}}=\overset{X^2}{\overset{|}{C}}-R^2 \qquad (I)$$

in which $R^1$ represents optionally substituted alkyl, optionally substituted alkenyl, optionally substituted cycloalkyl, optionally substituted aryl or represents optionally substituted heteroaryl, $R^2$ represents alkyl, halogenoalkyl, 1-hydroxyalkyl, 2-hydroxyalkyl, 1-hydroxyhalogenalkyl, 1-alkenyl or 2-alkenyl, $X^1$ represents fluorine, chlorine, bromine or iodine, $X^2$ represents fluorine, chlorine, bromine or iodine, and Y represents nitrogen or a CH group, and addition products thereof with acids or metal salts are very active as microbicides in plant protection and in the protection of materials.

12 Claims, No Drawings

HALOGEN ALKENYL AZOLYL MICROBICIDES

The present invention relates to novel halogenoalkenyl-azolyl derivatives, to a process for their preparation and to their use as microbicides in plant protection and in the protection of materials.

It has already been disclosed that certain halogenoallyl-azolyl derivatives possess fungicidal properties (cf. EP-0 097 425 and EP-A 0 440 949). Thus, for example, 4-(1-chloro-cyclopropyl)-1,1,2-trichloro-4-hydroxy-5-(1,2,4triazol-1-yl)-pent-1-ene can be employed for combating fungi. The action of this substance is good, but in some cases leaves something to be desired at low application rates.

Novel halogenoalkenyl-azolyl derivatives have now been found of the formula

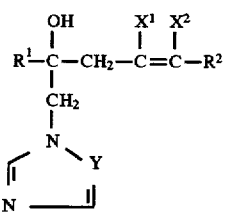 (I)

in which

R$^1$ represents optionally substituted alkyl, optionally substituted alkenyl, optionally substituted cycloalkyl, optionally substituted aryl or represents optionally substituted heteroaryl, R$^2$ represents alkyl, halogenoalkyl, 1-hydroxyhalogenoalkyl, 1-hydroxyalkyl, 2-hydroxyalkyl, 1-alkenyl or 2-alkenyl, X$^1$ represents fluorine, chlorine, bromine or iodine, X$^2$ represents fluorine, chlorine, bromine or iodine, and Y represents nitrogen or a CH group, and their acid addition salts and metal salt complexes.

The compounds of the formula (I) contain an asymmetrically substituted carbon atom and can therefore be obtained in both optical isomer forms. Furthermore, depending on the position of the substituents around the double bond, the substances of the formula (I) may exist in two geometrical isomer forms. The present invention relates both to the isomer mixtures and to the individual isomers.

It has additionally been found that halogenoalkenyl-azolyl derivatives of the formula (I) and their acid addition salts and metal salts are obtained if alkines of the formula

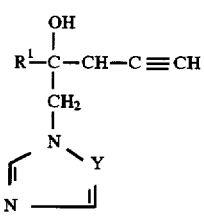 (II)

in which

R$^1$ and Y have the meaning given above, are initially reacted in a first stage with strong bases in the presence of a diluent, and the resulting substances are then either a) reacted with compounds of the formula

R$^3$—Z (III)

in which

R$^3$ represents alkyl or halogenoalkyl and

Z represents chlorine, bromine, iodine, methylsulphonyloxy or 4-methylphenylsulphonyloxy, in the presence of a diluent, or b) reacted with carbonyl compounds of the formula

 (IV)

in which

R$^4$ represents hydrogen, alkyl or halogenoalkyl and

R$^5$ represents hydrogen or alkyl, optionally in the presence of a diluent, or c) reacted with oxiranes of the formula

 (V)

in which

R$^6$ represents hydrogen or alkyl and

R$^7$ represents hydrogen or alkyl, optionally in the presence of a diluent, and in a second stage the resulting azolyl-alkine derivatives of the formula

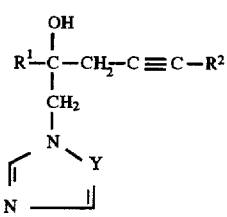 (VI)

in which

R$^1$, R$^2$ and Y have the meanings given above, are reacted with halogen or halogen-donor compounds in the presence of a diluent, or d) halogenoalkenyl-azolyl derivatives of the formula

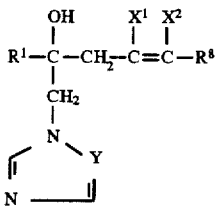 (Ia)

in which

R$^1$, X$^1$, X$^2$ and Y have the meanings given above and R$^8$ represents 1-hydroxyalkyl or 2-hydroxyalkyl, are reacted with thionyl chloride in the presence of a diluent and if desired are then treated with an acid-binding agent, and, if desired, an acid or a metal salt is then added on to the compounds of the formula (I) thus obtained.

Finally, it has been found that the novel halogenoalkenyl-azolyl derivatives of the formula (I) and their acid addition salts and metal salt complexes possess strong microbicidal properties and can be employed both in plant protection and in the protection of materials.

Surprisingly, the substances according to the invention possess a better microbicidal activity, in both plant protection and the protection of materials, than the previously known compounds of the same general mode of action which are closest to them in terms of constitution. Thus in their fungicidal properties the substances according to the invention exceed, for example, 4-(1-chloro-cyclopropyl)-1, 1,2-trichloro-4-hydroxy-5-(1,2,4triazol-1-yl)pent-1-ene.

A general definition of the halogenoalkenyl-azolyl derivatives according to the invention is given by the formula (I).

$R^1$ preferably represents straight-chain or branched alkyl having 1 to 6 carbon atoms, it being possible for each of these radicals to be monosubstituted to trisubstituted by identical or different substituents consisting of halogen, cycloalkyl having 3 to 7 carbon atoms, phenyl and/or halogenophenyl, or represents alkenyl having 2 to 6 carbon atoms, it being possible for each of these radicals to be monosubstituted to trisubstituted by identical or different substituents consisting of halogen, phenyl and/or halogenophenyl, or represents cycloalkyl having 3 to 7 carbon atoms, it being possible for each of these cycloalkyl radicals to be monosubstituted to trisubstituted by identical or different substituents consisting of halogen and/or alkyl having 1 to 4 carbon atoms, or represents phenyl which can be monosubstituted to trisubstituted by identical or different substituents consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents an optionally benzo-fused five- or six-membered heteroaromatic radical having 1 to 3 heteroatoms such as nitrogen, sulphur and/or oxygen, it being possible for each of these radicals to be monosubstituted to trisubstituted by identical or different substituents consisting of halogen, alkyl having 1 to 4 carbon atoms, hydroxyalkyl having 1 to 4 carbon atoms, hydroxyalkinyl having 3 to 8 carbon atoms, alkoxy having 1or 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine atoms or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano.

$R^2$ preferably represents straight-chain or branched alkyl having 1 to 6 carbon atoms, straight-chain or branched halogenoalkyl having 1 to 6 carbon atoms and 1 to 5 fluorine atoms and/or chlorine atoms, or represents straight-chain or branched 1-hydroxyalkyl having 1 to 6 carbon atoms, or represents straight-chain or branched 2-hydroxyalkyl having 2 to 6 carbon atoms, straight-chain or branched 1-hydroxyhalogenoalkyl having 1 to 6 carbon atoms and 1 to 3 halogen atoms, or represents straight-chain or branched 1-alkenyl having 2 to 6 carbon atoms, or represents straight-chain or branched 2-alkenyl having 2 to 6 carbon atoms.

$X^1$ also preferably represents fluorine, chlorine, bromine or iodine.

$X^2$ also preferably represents fluorine, chlorine, bromine or iodine. Y also preferably represents a nitrogen atom or a CH group.

$R^1$ particularly preferably represents methyl, ethyl, n-propyl, isopropyl, n-butyl, sec-butyl, i-butyl, tert-butyl, tert-pentyl, 1-ethyl-1-methyl-propyl, 1,1-dimethyl-pentyl, 1,1,2-trimethylpropyl or 1,1-dimethyl-prop-2-enyl, it being possible for each of these aforementioned radicals to be monosubstituted to trisubstituted by identical or different substituents consisting of fluorine, chlorine, bromine, phenyl, chlorophenyl, dichlorophenyl, fluorophenyl and/or difluorophenyl, or represents 1-methyl-cyclohexyl, cyclohexyl, 1-chloro-cyclopropyl, 1-methylcyclopropyl, cyclopropyl, 1-methylcyclopentyl, cyclopentyl or 1-ethylcyclopentyl, or represents phenyl which can be monosubstituted to trisubstituted by identical or different substituents consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and/or cyano, or represents pyrazolyl, imidazolyl, 1,2,4triazolyl, pyrrolyl, furanyl, thienyl, thiazolyl, oxazolyl, pyridinyl, pyrimidinyl, triazinyl, quinolyl, isoquinolyl, quinazolinyl, indolyl, benzothienyl, benzofuranyl, benzothiazolyl or benzimidazolyl, it being possible for each of these radicals to be monosubstituted to trisubstituted by identical or different substituents consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximino-ethyl, nitro, cyano, formyl, dimethoxymethyl, acetyl and/or propionyl.

$R^2$ particularly preferably represents methyl, ethyl, n-propyl, i-butyl, n-butyl, n-pentyl, chloromethyl, fluoromethyl, 2-chloroethyl, 2-fluoroethyl, 3-chloropropyl, 3-fluoropropyl, trichloromethyl, trifluoromethyl, hydroxymethyl, 1-hydroxyethyl, 1-hydroxy-propyl, 1-hydroxy-butyl, 2-hydroxy-prop-2-yl, 3-hydroxy-but-2-yl, 3-hydroxy-pent-3-yl, 2-hydroxy-ethyl, 2-hydroxy- 1-propyl, 2-hydroxy-2-methylpropyl, 2-hydroxy-1-butyl, 1-hydroxy-2,2,2-trichloro-ethyl, vinyl, 1-propenyl, 1-butenyl, 2-butenyl, 1-propen-2-yl or 2-buten-2-yl.

$X^1$ also particularly preferably represents fluorine, chlorine, bromine or iodine.

$X^2$ also particularly preferably represents fluorine, chlorine, bromine or iodine.

Y also particularly preferably represents a nitrogen atom or a CH group.

Other preferred compounds according to the invention are adducts of acids and those halogenoalkenylazolyl derivatives of the formula (I) in which $R^1$, $R^2$, $X^1$, $X^2$ and Y have those meanings which have been mentioned as preferable for these substituents.

The acids which can be added on preferably include hydrohalic acids, for example hydrochloric acid and hydrobromic acid, especially hydrochloric acid, and also phosphoric acid, nitric acid, mono- and bifunctional carboxylic acids and hydroxycarboxylic acids, for example acetic acid, maleic acid, succinic acid, fumaric acid, tartaric acid, citric acid, salicylic acid, sorbic acid and lactic acid, and also sulphonic acids, for example p-toluenesulphonic acid and 1,5-naphthalenedisulphonic acid, and also saccharin and thiosaccharin.

Other preferred compounds according to the invention are adducts of salts of metals of main groups II to IV and of subgroups I and II and IV to VIII of the Periodic Table of the Elements and those halogenoalkenyl-azolyl derivatives of the formula (I) in which $R^1$, $R^2$, $X^1$, $X^2$ and Y have those meanings which have been mentioned as preferable for these substituents.

In this context, salts of copper, zinc, manganese, magnesium, tin, iron and nickel are particularly preferred. Suitable anions of these salts are those derived from acids which lead to physiologically acceptable adducts. Particularly preferred such acids in this context are the hydrohalic acids, for example hydrochloric acid and hydrobromic acid, and also phosphoric acid, nitric acid and sulphuric acid.

Examples of substances according to the invention which may be mentioned are the halogenoalkenyl-azolyl derivatives listed in the table below.

TABLE 1

$$R^1-\underset{\underset{\underset{\underset{N\diagdown\atop \parallel\diagdown Y}{N\diagdown\phantom{xx}\diagup}}{CH_2}}{|}}{\overset{OH}{\underset{|}{C}}}-CH_2-\overset{X^1}{\underset{|}{C}}=\overset{X^2}{\underset{|}{C}}-R^2 \quad (I)$$

| $R^1$ | $X^1$ | $X^2$ | $R^2$ | Y |
|---|---|---|---|---|
| $-C(CH_3)_3$ | Cl | Cl | $-C_2H_5$ | N |
| $-C(CH_3)_3$ | Br | Br | $-C_2H_5$ | N |
| $-C(CH_3)_3$ | F | F | $-C_3H_7\text{-n}$ | N |
| $-C(CH_3)_3$ | I | I | $-C_2H_5$ | N |
| $-\underset{CH_3}{\overset{CH_3}{\underset{|}{\overset{|}{C}}}}-CH(CH_3)_2$ | Cl | Cl | $-C_2H_5$ | N |
| $-\underset{CH_3}{\overset{CH_3}{\underset{|}{\overset{|}{C}}}}-C_2H_5$ | Br | Br | $-CH_3$ | N |
| $-\underset{CH_3}{\overset{CH_3}{\underset{|}{\overset{|}{C}}}}-CH=CH_2$ | Cl | Cl | $-C_2H_5$ | N |
| cyclohexyl-CH$_3$ | Cl | Cl | $-C_2H_5$ | N |
| cyclopentyl-CH$_3$ | Cl | Cl | $-C_4H_9\text{-n}$ | N |

TABLE 1-continued $$R^1-\underset{\underset{\underset{\underset{N\diagdown\atop \parallel\diagdown Y}{N\diagdown\phantom{xx}\diagup}}{CH_2}}{|}}{\overset{OH}{\underset{|}{C}}}-CH_2-\overset{X^1}{\underset{|}{C}}=\overset{X^2}{\underset{|}{C}}-R^2 \quad (I)$$

| $R^1$ | $X^1$ | $X^2$ | $R^2$ | Y |
|---|---|---|---|---|
| cyclopentyl-C$_2$H$_5$ | Cl | Cl | $-C_2H_5$ | N |
| $-\underset{CH_3}{\overset{CH_3}{\underset{|}{\overset{|}{C}}}}-\text{phenyl}$ | Cl | Cl | $-C_2H_5$ | N |
| $-\underset{CH_3}{\overset{CH_3}{\underset{|}{\overset{|}{C}}}}-CH_2F$ | Cl | Cl | $-C_2H_5$ | N |
| $-\underset{CH_2F}{\overset{CH_2F}{\underset{|}{\overset{|}{C}}}}-CH_3$ | Cl | Cl | $-C_2H_5$ | N |
| $-C(CH_3)_3$ | Br | Br | $-CH_2-\underset{}{\overset{CH_3}{\underset{|}{CH}}}-CH_3$ | N |
| $-C(CH_3)_3$ | Br | Br | $-CH_2-C(CH_3)_3$ | N |
| $-C(CH_3)_3$ | Br | Br | $-CH_2OH$ | N |
| $-C(CH_3)_3$ | Cl | Cl | $-CH-OH$ $\phantom{xxx}|$ $\phantom{xxx}CH_3$ | N |
| $-C(CH_3)_3$ | Cl | Cl | $-CH_2-CH_2-OH$ | N |
| $-C(CH_3)_3$ | Cl | Cl | $-\underset{CH_3}{\overset{CH_3}{\underset{|}{\overset{|}{C}}}}-OH$ | N |
| $-C(CH_3)_3$ | Cl | Cl | $-CH_2-CH-OH$ $\phantom{xxxxxxx}|$ $\phantom{xxxxxxx}CH_3$ | N |
| $-C(CH_3)_3$ | Cl | Cl | $-CH_2-\underset{CH_3}{\overset{CH_3}{\underset{|}{\overset{|}{C}}}}-OH$ | N |
| $-\underset{CH_3}{\overset{CH_3}{\underset{|}{\overset{|}{C}}}}-CH_2Cl$ | Cl | Cl | $C_2H_5$ | N |
| $-\underset{CH_3}{\overset{CH_3}{\underset{|}{\overset{|}{C}}}}-CH=CH-Cl$ | Cl | Cl | $C_2H_5$ | N |
| $-\underset{CH_2Cl}{\overset{CH_2Cl}{\underset{|}{\overset{|}{C}}}}-CH_3$ | Cl | Cl | $C_2H_5$ | N |

TABLE 1-continued $$R^1-\underset{\underset{\underset{N\diagup\diagdown Y}{\overset{|}{CH_2}}}{\overset{|}{C}}}{\overset{OH}{|}}-CH_2-\underset{}{\overset{X^1}{C}}=\underset{}{\overset{X^2}{C}}-R^2 \quad (I)$$

| $R^1$ | $X^1$ | $X^2$ | $R^2$ | Y |
|---|---|---|---|---|
| 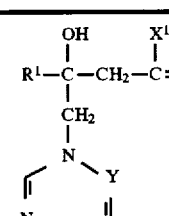 | Cl | Cl | $C_2H_5$ | N |
| 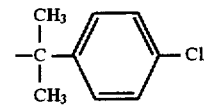 | Cl | Cl | $C_2H_5$ | N |
| 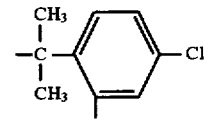 | Cl | Cl | $C_2H_5$ | N |
| 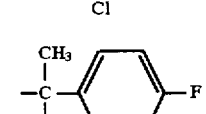 | Cl | Cl | $C_2H_5$ | N |
| 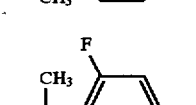 | Br | Br | $-CH_3$ | N |
| 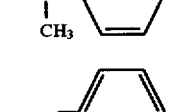 | Br | Br | $C_2H_5$ | N |
| 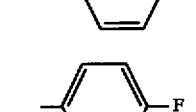 | Cl | Cl | $C_2H_5$ | N |
| 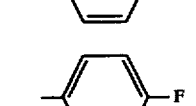 | Cl | Cl | $C_2H_5$ | N |
| 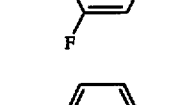 | Cl | Cl | $C_2H_5$ | CH |
| 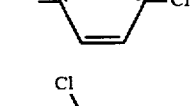 | Cl | Cl | $C_2H_5$ | N |
| 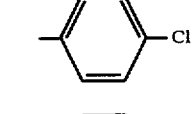 | Cl | Cl | $C_2H_5$ | N |
| 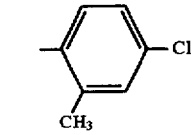 | Br | Br | $C_2H_5$ | N |
|  | Cl | Cl | $CH_3$ | N |
| 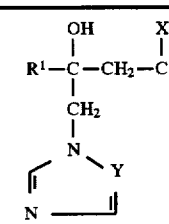 | Cl | Cl | $C_2H_5$ | N |
| 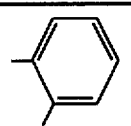 | Cl | Cl | $C_2H_5$ | N |
| 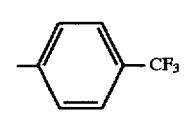 | Cl | Cl | $C_2H_5$ | N |
| 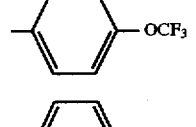 | Cl | Cl | $C_2H_5$ | N |
| 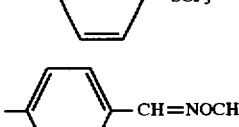 | Cl | Cl | $C_2H_5$ | N |
| 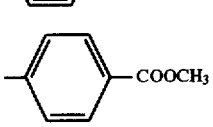 | Cl | Cl | $C_2H_5$ | N |
| 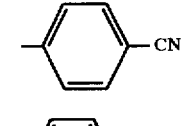 | Cl | Cl | $C_2H_5$ | N |
| 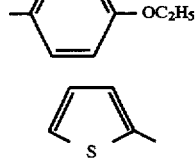 | Cl | Cl | $C_2H_5$ | N |

TABLE 1-continued $$R^1-\underset{\underset{\underset{\underset{N}{\parallel}}{N\diagdown N}}{\overset{|}{CH_2}}}{\overset{\overset{OH}{|}}{C}}-CH_2-\overset{\overset{X^1}{|}}{C}=\overset{\overset{X^2}{|}}{C}-R^2 \quad (I)$$

| R¹ | X¹ | X² | R² | Y |
|---|---|---|---|---|
| 3-pyridyl | Cl | Cl | C₂H₅ | N |
| pyrazol-1-yl | Cl | Cl | C₂H₅ | N |
| pyrazol-1-yl | Cl | Cl | C₂H₅ | N |
| 2-quinolinyl | Cl | Cl | C₂H₅ | N |
| 1-chlorocyclopropyl | Cl | Cl | CH₂Cl | N |
| 1-chlorocyclopropyl | Cl | Cl | —CH₂—CH₂—Cl | N |
| 1-chlorocyclopropyl | Cl | Cl | —CH=CH₂ | N |
| —C(CH₃)₃ | Cl | Cl | —CH=CH₂ | CH |
| —C(CH₃)₃ | Cl | Cl | —C(CH₃)=CH₂ | N |

Using in the first stage 4-(1-chloro-cyclopropyl)-4hydroxy-5-(1,2,4-triazol-1-yl)-1-pentine as starting material, butyl-lithium as strong base and methyl iodide as reaction component and reacting the resulting substance in the second stage with bromine, the course of the process according to the invention in accordance with variant (a) can be illustrated by the following formula scheme:

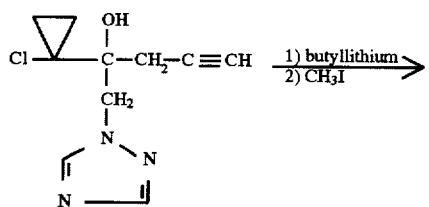

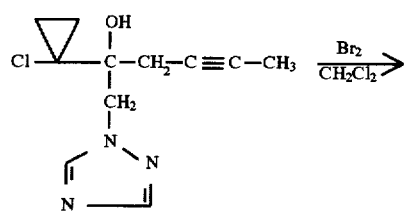

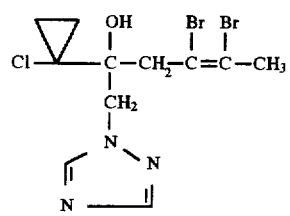

Using in the first stage 4-(1-chloro-cyclopropyl)-4hydroxy-5-(1,2,4-triazol-1-yl)-1-pentine as starting material, butyl-lithium as strong base and formaldehyde as reaction component and reacting the resulting substance in the second stage with bromine, the course of the process according to the invention in accordance with variant (b) can be illustrated by the following formula scheme:

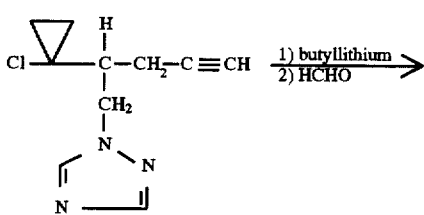

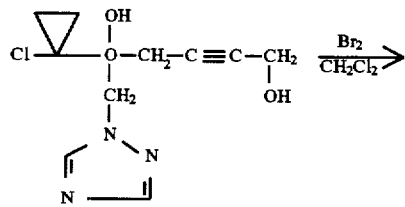

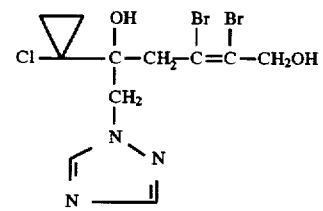

Using in the first stage 4(1-chloro-cyclopropyl)4hydroxy-5-(1,2,4-triazol-1-yl)-1-pentine as starting material, butyl-lithium as strong base and oxirane as reaction component and reacting the resulting substance in the second stage with bromine, the course of the process according to the invention in accordance with variant (c) can be illustrated by the following formula scheme:

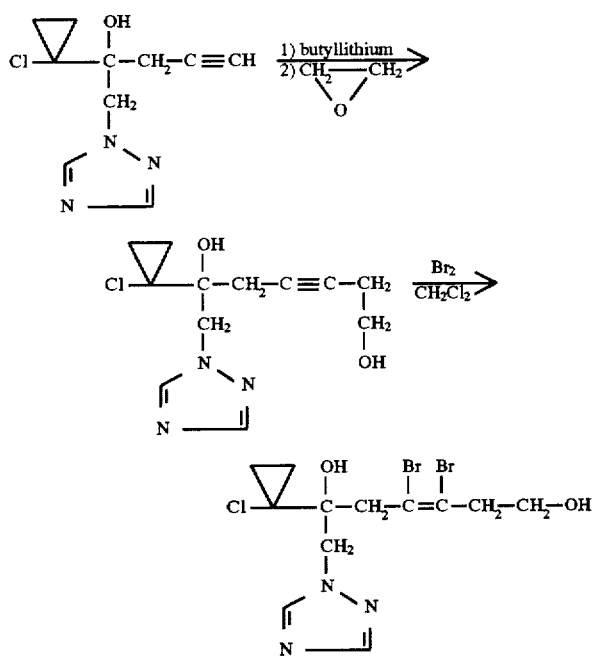

Using 6-(1-chlorocyclopropyl)-3,4-dichloro-2,6-dihydroxy-2-methyl-7-(1,2,4-triazol-1-yl)-hept-3-ene as starting substance and thionyl chloride as reaction component, the course of the process according to the invention in accordance with variant (d) can be illustrated by the following formula scheme:

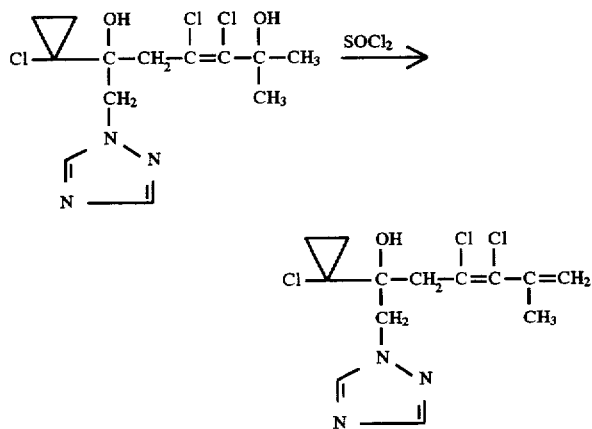

A general definition of the alkines required as starting materials when carrying out the process according to the invention is given by the formula (II). In this formula, $R^1$ and Y preferably have those meanings which have already been mentioned as preferable for these radicals in connection with the description of the substances of the formula (I) according to the invention.

The alkines of the formula (II) are known or can be prepared in a simple manner by known methods (cf. EP-A 0 353 558, EP-A 0 440 949 and EP-A 0 440 950).

Suitable bases when carrying out the first stage of the process according to the invention are all strong alkali metal bases which are customary for such metallation reactions. Preferred possibilities for use are butyllithium, lithium diisopropylamide, sodium hydride, sodium amide and potassium tert-butylate.

When carrying out the first stage of the process according to the invention, suitable diluents for the metallation reaction are all those which are customary for such reactions. Preferred possibilities for use are ethers, such as tetrahydrofuran, dioxane, diethyl ether and 1,2-dimethoxyethane, and also liquid ammonia or else strongly polar solvents, such as dimethyl sulphoxide.

When carrying out the metallation in the first stage of the process according to the invention the reaction temperatures can be varied within a certain range. The procedure is in general carried out at temperatures between −70° C. and 0° C., preferably at temperatures between −60° C. and 0° C.

All steps of the process according to the invention are generally carried out under atmospheric pressure.

When carrying out the metallation in the first stage of the process according to the invention, from 2 to 3 equivalents, preferably from 2.0 to 2.5 equivalents, of strong base are generally employed per mole of alkine of the formula (II). The reaction is generally performed under an inert gas atmosphere, for example under nitrogen or argon. The reaction mixture is generally used for the subsequent synthesis without being worked up.

A general definition of the compounds required as reaction components when carrying out variant (a) in the first stage of the process according to the invention is given by the formula (III).

$R^3$ preferably represents straight-chain or branched alkyl having 1 to 6 carbon atoms, straight-chain or branched halogenoalkyl having 1 to 6 carbon atoms and 1 to 5 fluorine and/or chlorine atoms.

Z also preferably represents chlorine, bromine, iodine, methylsulphonyloxy or 4-methyl-phenyl-sulphonyloxy.

$R^3$ particularly preferably represents methyl, ethyl, n-propyl, i-butyl, n-butyl, n-pentyl, chloromethyl, fluoromethyl, 2-chloroethyl, 2-fluoroethyl, 3-chloropropyl, 3-fluoropropyl, trichloromethyl, trifluoromethyl.

Z also particularly preferably represents chlorine, bromine, iodine, methylsulphonyloxy or 4-methyl-phenyl-sulphonyloxy.

The compounds of the formula (III) are known.

When carrying out variant (a) in the first stage of the process according to the invention, suitable diluents are all organic solvents which are customary for such reactions. Preferred possibilities for use are those diluents which were mentioned as preferable in connection with the metallation reaction.

When carrying out variant (a) in the first stage of the process according to the invention the reaction temperatures can be varied within a certain range. The procedure is in general carried out at temperature between −40° C. and +50° C., preferably between −40° C. and room temperature.

When carrying out variant (a) in the first stage of the process according to the invention, the quantities of the reaction components are chosen such that in general from 1 to 1.5 mol, preferably from 1 to 1.3 mol, of compound of the formula (III) is present per mole of metallated alkine. To this end the reaction mixture obtained in the metallation is generally employed without being worked up beforehand. After the reaction has been carried out in accordance with variant (a), working up takes place by customary methods. The general procedure is to dilute the reaction mixture with an organic solvent of low miscibility with water, to wash, dry and concentrate the organic phase and to purify further the residue which remains by either recrystallization or chromatography. However, it is also possible to concentrate the reaction mixture after the end of the reaction and to free the residue which remains, by recrystallization or chromatography, from any impurities still present.

A general definition of the carbonyl compounds required as reaction components when carrying out variant (b) in the first stage of the process according to the invention is given by the formula (IV).

$R^4$ preferably represents hydrogen, straight-chain or branched alkyl having 1 to 5 carbon atoms or straight-chain or branched halogenoalkyl having 1 to 5 carbon atoms and 1 to 3 halogen atoms.

$R^5$ preferably represents hydrogen or straight-chain or branched alkyl having 1 to 5 carbon atoms.

$R^4$ particularly preferably represents hydrogen, methyl ethyl, propyl or trichloromethyl.

$R^5$ particularly preferably represents hydrogen, methyl, ethyl or propyl.

The carbonyl compounds of the formula (IV) are known.

Suitable diluents when carrying out variant (b) in the first stage of the process according to the invention are all organic solvents which are customary for such reactions. Preferred possibilities for use are those diluents which have been mentioned as preferable in connection with the metallation reaction.

When carrying out variant (b) in the first stage of the process according to the invention, the reaction temperatures and the other reaction conditions correspond to those also employed when carrying out variant (a).

A general definition of the oxiranes required as reaction components when carrying out variant (c) in the first stage of the process according to the invention is given by the formula (V).

$R^6$ preferably represents hydrogen or alkyl having 1 to 4 carbon atoms.

$R^7$ preferably represents hydrogen or alkyl having 1 to 4 carbon atoms.

$R^6$ particularly preferably represents hydrogen, methyl, ethyl or propyl.

$R^7$ particularly preferably represents hydrogen, methyl, ethyl or propyl.

The oxiranes of the formula (V) are known.

Suitable diluents when carrying out variant (c) in the first stage of the process according to the invention are all organic solvents which are customary for such reactions. Preferred possibilities for use are those diluents which have been mentioned as preferable in connection with the metallation reaction.

When carrying out variant (c) in the first stage of the process according to the invention, the reaction temperatures and the other reaction conditions correspond to those also employed when carrying out variant (a).

Suitable halogens when carrying out the second stage of the process according to the invention are preferably fluorine, chlorine, bromine and iodine as reaction components, and also mixed halogens, such as chlorine(I) fluoride, bromine(I) fluoride, iodine(I) fluoride, bromine(I) chloride, iodine(I) chloride or iodine(I) bromide (see Methodicium Chimicium, F. Korte, Vol. 7, p. 842 (1976)).

Examples of halogen-donor compounds which can be used are sulphuryl chloride, N-bromosuccinimide with hydrochloric acid, N-chlorosuccinimide with hydrobromic acid or N-chlorosuccinimide with hydrogen fluoride/pyridine (see Synthesis 1973, 780).

The addition reaction of the halogens onto the alkines of the formula (VI) can be promoted by the action of light, by heat, by radical-forming substances, such as organic peroxides, by surface-active substances, such as active charcoal, or metal salts, such as copper(II) chloride or iron(III) chloride. In some cases, the isomer ratio (E/Z) can be influenced by this means (see Houben-Weyl, Methoden der Org. Chemie [Methods of Organic Chemistry], Vol. V/3, p. 551 (1962)).

Suitable diluents when carrying out the second stage of the process according to the invention are all inert organic solvents which are customary for such reactions. Preferred possibilities for use are halogenated aliphatic hydrocarbons, such as methylene chloride, chloroform and carbon tetrachloride.

When carrying out the second stage of the process according to the invention the temperatures can be varied within a certain range. The procedure is in general carried out at temperatures between $-10°$ C. and $+120°$ C., preferably between $-5°$ C. and $+80°$ C.

When carrying out the second stage of the process according to the invention, an equivalent quantity or an excess of halogen or halogen-donor compound is generally employed per mole of alkine of the formula (VI). Working up takes place by customary methods. The general procedure is to dilute the reaction mixture with an organic solvent of low solubility in water, to wash the diluted mixture with water and to dry and then concentrate the organic phase. However, it is also possible to concentrate the reaction mixture directly after reaction has ended, by stripping off the volatile components under reduced pressure. The products which are formed can if desired be purified further by customary methods.

When carrying out variant (d) of the process according to the invention, starting materials used are halogenoalkenylazolyl derivatives of the formula (Ia), which can be prepared in accordance with variants (b) or (c) of the process according to the invention.

When carrying out the process according to the invention in accordance with variant (d), suitable diluents are all inert organic solvents which are customary for such reactions. Preferred possibilities for use are halogenated aliphatic hydrocarbons, such as methylene chloride, chloroform and carbon tetrachloride.

Suitable acid-binding agents when carrying out the process according to the invention in accordance with variant (d) are all inorganic or organic bases which can customarily be used for the elimination of hydrogen chloride. Preferred possibilities for use are alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium hydrogen carbonate, sodium hydrogen carbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out the process according to the invention in accordance with variant (d) the temperatures can be varied within a relatively large range. In the case of reaction with thionyl chloride, the procedure is in general carried out at temperatures between $0°$ C. and $80°$ C., preferably between $20°$ C. and $60°$ C. In the case of the elimination of hydrogen chloride, which may be necessary, in the presence of an acid-binding agent, the procedure is in general carried out at temperatures between $0°$ C. and $100°$ C., preferably between $20°$ C. and $80°$ C.

When carrying out the process according to the invention in accordance with variant (d), an equivalent quantity or else an excess of thionyl chloride is generally employed per mole of halogenoalkenyl-azolyl derivative of the formula (I-a). If separate elimination of hydrogen chloride is necessary, then from 1 to 2 mol of acid-binding agent is employed per mole of chlorinated product. Working up takes place by customary methods.

The halogenoalkenyl-azolyl derivatives of the formula (I) which are obtainable according to the process of the invention can be converted into acid addition salts or metal salt complexes.

Suitable acids for the preparation of acid addition salts of the compounds of the formula (I) are preferably those which have already been mentioned as preferable acids in connection with the description of the acid addition salts according to the invention.

The acid addition salts of the compounds of the formula (I) can be obtained in a simple manner by customary methods of forming salts, for example by dissolving a compound of the formula (I) in an appropriate inert solvent and adding the acid, for example hydrochloric acid, and they can be isolated in a known manner, for example by filtration, and can if desired be purified by washing with an inert organic solvent.

Suitable salts for preparing metal salt complexes of the compounds of the formula (I) are preferably those metal salts which have already been mentioned as preferable metal salts in connection with the description of the metal salt complexes according to the invention.

The metal salt complexes of the compounds of the formula (I) can be obtained in a simple manner by customary methods, for example by dissolving the metal salt in alcohol, for example ethanol, and adding the solution to compounds of the formula (I). Metal salt complexes can be isolated in a known manner, for example by filtration, and can if desired be purified by recrystallization.

The active compounds according to the invention have a strong microbicidal action and can be employed for combating unwanted microorganisms, such as fungi and bacteria, in plant protection and in the protection of materials.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea;*
(conidia form: Drechslera, syn: Heiminthosporium);
Cochliobolus species, such as *Cochliobolus sativus;*
(conidia form: Drechslera, syn: Heiminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae;*
Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating diseases of cereals and rice, such as Pseudocercosporella, Erysiphe, Fusarium, Pyrenophora, Cochliobolus, Pyricularia and Pellicularia, and for combating Botrytis in fruit-growing, viticulture and vegetable-growing. Furthermore, they possess a good and broad in vitro action.

In the protection of materials, the substances according to the invention can be employed for protecting industrial materials against infestation and destruction by unwanted microorganisms.

Industrial materials in the present context are to be understood as meaning non-living materials which have been prepared for use in industry. Examples of industrial materials which are to be protected by active compounds according to the invention against microbial alteration or destruction are adhesives, sizes, paper and board, textiles, leather, wood, coating compositions and plastics articles, cooling lubricants and other materials which can be infested with or broken down by microorganisms. Within the context of the materials to be protected mention may also be made of parts of production plants, for example cooling-water circuits, which may be impaired by the multiplication of microorganisms. Within the scope of the present invention, industrial materials which may preferably be mentioned are adhesives, sizes, papers and boards, leather, wood, coating compositions, cooling lubricants and heat-transfer liquids, particularly preferably wood.

Examples of microorganisms which can bring about degradation or alteration of the industrial materials are bacteria, fungi, yeasts, algae and slime organisms. The active compounds according to the invention preferably act against fungi, especially moulds, wood-discolouring and wood-destroying fungi (Basidiomycetes) and against slime organisms and algae.

Microorganisms of the following genera may be mentioned by way of example:

Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*

Penicillium, such as *Penicillium glaucum*,
Polyporus, such as *Polyporus versicolor*,
Aureobasidium, such as *Aureobasidium pullulans*,
Sclerophoma, such as *Sclerophoma pityophila*,
Trichoderma, such as *Trichoderma viride*,
Escherichia, such as *Escherichia coli*,
Pseudomonas, such as *Pseudomonas aeruginosa*,
Staphylococcus, such as *Staphylococcus aureus*.

Depending on their particular physical and/or chemical properties, the active compounds can be converted into customary formulations, such as solutions, emulsions, suspensions, powders, foams, pastes, granules, aerosols, very fine capsules in polymeric substances and in coating compositions for seed, and ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents, such as alcohols, can, for example, also be used as auxiliaries. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in plant protection in general contain between 0.1 and 95 per cent by weight of active compound, preferably between 0.5 and 90%.

When used in plant protection the active compounds according to the invention can be employed in the formulations as a mixture with known fungicides, bactericides, acaricides, nematicides or insecticides, for example to widen the spectrum of action or to prevent the build-up of resistance.

Examples of substances for the mixtures are the following compounds.

Fungicides 2-aminobutane; 2-anilino4-methyl-6-cyclopropylpyrimidine; 2',6'-dibromo-2-methyl-4'-trifluoromethoxy4'-trifluoro-methyl-1,3-thiazole-5-carboxanilide; 2,6-dichloro-N-(4-trifluoromethylbenzyl)benzamide; (E)-2-methoximino-N-methyl-2-(2-phenoxyphenyl)-acetamide; 8-hydroxyquinoline sulphate; methyl (E)-2-{2-[6-(2-cyanophenoxy)-pyrimidin4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, dichlofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, firmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides
bronopol, dichlorophen, nitrapyrin, nickel dimethyldithiocarbamate, kasugamycin, octhilinone, furancarboxylic acid, oxytetracyclin, probenazole, streptomycin, teclofalam, copper sulphate and other copper preparations.

Insecticides/Acaricides/Nematicides
abamectin, abamectin, AC 303 630, acephate, acrinathrin, alanycarb, aldicarb, alphamethrin, amitraz, avermectin, AZ 60541, azadirachtin, azinphos A, azinphos M azocyclotin,

*Bacillus thuringiensis,* bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184 699, chloethocarb, chlorethoxyfos, chlorfenvinphos, chlorfluazuron, chlormephos, chlorpyrifos, chlorpyrifos M cis-resmethrin, clocythrin, clofentezine, cyanophos, cycloprothrin, cyfluthrin, cyhalothrin, cyhexatin, cypermethrin, cyromazine, deltamethrin, demeton-M demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, permethrin, phenthoate, phorate, phosalone, phosmet, phosphamdon, phoxim, pirimicarb, pirimiphos M pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

Also possible is a mixture with other known active compounds, such as herbicides, or with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active-compound concentrations in the use forms can be varied within a relatively large range: They are, in general, between 1 and 0.0001% by weight, preferably between 0.5 and 0.001% by weight. In the treatment of seed, amounts of active compound of 0.001 to 50 g per kilogram of seed, preferably 0.01 to 10 g, are generally required.

In the treatment of soil, active-compound concentrations of 0.00001 to 0.1% by weigh, preferably 0.0001 to 0.02% by weight, are required at the place of action.

The compositions used for protecting industrial materials contain the active substances in general in a quantity of from 1 to 95%, preferably from 10 to 75%.

The concentrations in which the active compounds according to the invention are employed depend on the nature and incidence of the microorganisms to be combated and on the composition of the material to be protected. The optimum amount for use can be determined by series of tests. In general, the use concentrations are in the range from 0.001 to 5% by weight, preferably from 0.05 to 1.0% by weight, relative to the material to be protected.

The activity and the spectrum of action of the active compounds to be used, in accordance with the invention, in the protection of materials, and/or of the compositions, concentrates or, quite generally, formulations which can be prepared therefrom, can be increased if other antimicrobially active compounds, fungicides, bactericides, herbicides, insecticides or other active compounds for enlarging the spectrum of action or for achieving particular effects, for example additional protection against insects, are added, optionally. These mixtures may possess a broader spectrum of action than the compounds according to the invention.

In many cases, synergistic effects are obtained in this case; in other words, the activity of the mixture is greater than the activity of the individual components. Examples of particularly favourable co-components are the following compounds:

sulphenamides such as dichlofluanid (Euparen), tolyfluanid (Methyleuparen), folpet, fluorfolpet;

benzimidazoles such as carbendazim (MBC), benomyl, fuberidazole, thiabendazole or salts thereof, thiocyanates, such as thiocyanatomethylthiobenzothiazole (TCMTB), methylenebisthiocyanate (MBT);

quaternary ammonium compounds such as benzyldimethyltetradecylammonium chloride, benzyl-dimethyl-dodecyl-ammonium chloride, dodecyl-dimethyl-ammonium chloride;

morpholine derivatives, such as $C_{11}$–$C_{14}$-4-alkyl-2,6-dimethyl-morpholine homologues (tridemorph), (±)-cis-4-[tert-butylphenyl)-2-methylpropyl]-2,6-dimethylmorpholine (fenpropimorph), falimorph;

phenols, such as o-phenylphenol, tribromophenol, tetrachlorophenol, pentachlorophenol, 3-methyl4-chlorophenol, dichlorophen, chlorophen or salts thereof;

azoles, such as triadimefon, triadimenol, bitertanol, tebuconazole, propiconazole, azaconazole, hexaconazole, prochloraz cyproconazole of 1-(2-chlorophenyl)-2-(1,2,4-triazol-1-yl-methyl)-3,3-dimethyl-butan-2-ol.

iodopropargyl derivatives, such as iodopropargyl butyl-carbamate (IPBC), iodopropargyl chlorophenyl formal, iodopropargyl phenylcarbamate, iodopropargyl hexylcarbamate, iodopropargyl cyclohexylcarbamate, iodopropargyl oxyethyl phenylcarbamate;

iodine derivatives, such as diiodomethyl p-aryl sulphones, for example diiodomethyl p-tolyl sulphone;

bromine derivatives, such as bromopol;

isothiazolines, such as N-methylisothiazolin-3-one, 5-chloro-N-methylisothiazolin-3-one, 4,5-dichloro-N-octylisothiazolin-3-one, N-octylisothiazolin-3-one (octilinone);

benzisothiazolinones, cyclopenteneisothazolines;

pyridines, such as 1-hydroxy-2-pyridinethione (and its Na, Fe, Mn, Zn salts), tetrachloro-4-methylsulphonylpyridine;

metal soaps, such as tin, copper and zinc naphthenate, octoate, 2-ethylhexanoate, oleate, phosphate and benzoate, and oxides such as TBTO, $Cu_2O$, CuO, ZnO; organic tin compounds, such as tributyltin naphthenate and tributyltin oxide;

dialkyldithiocarbamates, such as Na salts and Zn salts of dialkyldithiocarbamates, tetramethyltiuram disulphide (TMTD);

nitriles, such as 2,4,5,6-tetrachloroisophthalonitrile (chlorothalonil) and other microbicides having an activated halogen group, such as Cl-Ac, MCA, tectamer, bromopol, bromidox;

benzothiazoles such as 2-mercaptobenzthiazole; see dazomet above;

quinolines, such as 8-hydroxyquinoline;

formaldehyde donor compounds, such as benzyl alcohol mono(poly)hemiformal, oxazolidines, hexahydro-s-triazines, N-methylolchloroacetamide;

tris-N-(cyclohexyldiazeniumdioxy)-aluminium, N-(cyclohexyldiazeniumdioxy)-tributyltin and K salts, bis-(N-cyclohexyl)diazinium-(dioxy-copper or aluminium).

Insecticides preferably added are:

phosphoric esters such as azinphos-ethyl, azinphos-methyl, 1-(4-chlorophenyl)-4-(O-ethyl, S-propyl) phosphoryloxypyrazole (TIA-230), chlorpyrifos, coumaphos, demeton, demeton-S-methyl, diazinon, dichlorfos, dimethoate, ethoprophos, etrimfos, fenitrothion, fention, heptenophos, parathion, parathion-methyl, phosalone, phoxim, pirimiphos-ethyl, pirmiphos-methyl, profenofos, prothiofos, sulprofos, triazophos and trichlorophon.

Carbamates, such as aldicarb, bendiocarb, BPMC (2-(1-methylpropyl)phenyl methylcarbamate), butocarboxim, butoxycarboxim, carbaryl, carbofuran, carbosulfan, cloethocarb, isoprocarb, methomyl, oxamyl, pirimicarb, promecarb, propoxur and thiodicarb.

Pyrethroids, such as allethrin, alphamethrin, bioresmethrin, byfenthrin (FMC 54800), cycloprothrin, cyfluthrin, decamethrion, cyhalothrin, cypermethrin, deltamethrin, alpha-cyano-3-phenyl-2-methylbenzyl 2,2-dimethyl-3-(2-chloro-2-trifluoromethylvinyl) cyclopropanecarboxylate, fenpropathrin, fenfludirin, fenvalerate, flucythrinate, flumethrin, fluvalinate, permethrin and resmethrin; nitroimino and nitromethylene compounds, such as 1-[(6-chloro-3-pyridinyl)-methyl]4,5-dihydro-N-nitro-1H-imidazol-2-amine (imidachloprid).

Organosilicon compounds, preferably dimethyl(phenyl) silylmethyl 3-phenoxybenzyl ethers, such as dimethyl-(4-ethoxyphenyl)silylmethyl 3-phenoxybenzyl ether, or dimethyl(phenyl)-silylmethyl 2-phenoxy-6-pyridylmethyl ethers, for example dimethyl (9-ethoxyphenyl)silylmethyl 2-phenoxy-6-pyridylmethyl ether, or (phenyl)[3-(3-phenoxyphenyl)propyl](dimethyl)-silanes, for example (4-ethoxyphenyl)-[3(4-fluoro-3-phenoxyphenyl)-propyl] dimethylsilane.

Other active compounds which come into consideration are algicides, molluscicides, and active compounds against sea animals which populate, for example, the coatings of ships' hulls.

The preparation and the use of active compounds according to the invention are illustrated by the following examples.

PREPARATION EXAMPLE

Example 1

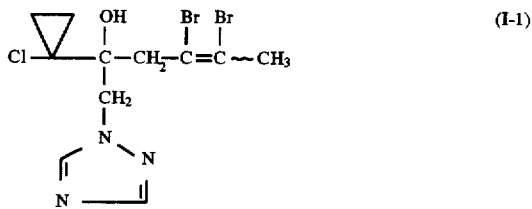

1st stage

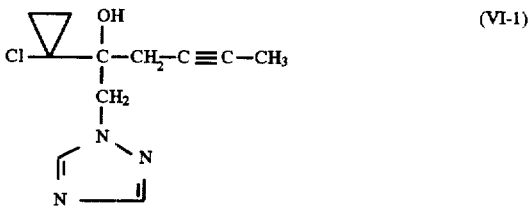

26.9 ml (63 mmol) of n-butyllithium in hexane are added at −30° C., with stirring under and a nitrogen atmosphere, to a mixture of 6.76 g (30 mmol) of 4-(1-chlorocyclopropyl) 4-hydroxy-5-(1,2,4-triazol-1-yl)-1-pentine and 60 ml of absolute tetrahydrofuran. After the end of the addition, stirring is continued at 0° C. for 15 minutes, and then a solution of 4.68 g (33 mmol) of methyl iodide in 30 ml of absolute tetrahydrofuran is added dropwise. Stirring is then continued for an hour at 20° C. The reaction mixture is worked up by diluting with ethyl acetate and subjecting it several times to extraction by shaking with saturated aqueous ammonium chloride solution. The organic phase is dried over sodium sulphate and filtered and the filtrate is concentrated under reduced pressure. This gives 7.2 g of a product which consists to the extent of 67.6% of 5-(1-chlorocyclopropyl)-5-hydroxy-6-(1,2,4triazol-1-yl-2-hexine. For purification, the product is chromatographed on silica gel using ethyl acetate. 4.8 g (67% of theory) of 5-(1-chlorocyclopropyl)-5-hydroxy-6-(1,2,4-triazol-1-yl)-2-hexine are obtained in the form of an oil.

$H^1$-NMR (200 MHz $CDCl_3$): δ=0.4–1.2 (m, 4H); 1.8 (t, 3H); 2.65 (m, 2H; 4.2 (OH); 4.65 (AB system, 2H);8.0 (s, 1H); 8.3 (s, 1H) ppm.

2nd stage

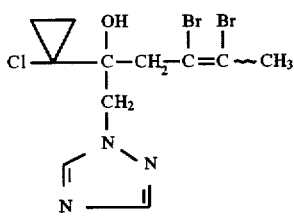
(I-1)

A solution of 32.0 g (0.2 mol) of bromine in 400 ml of absolute dichloromethane is added dropwise over the course of 3 hours at between 0° C. and 5° C. with stirring to a mixture of 47.9 g (0.2 mol) of 5-(1-chlorocyclopropyl)-5-hydroxy-6-(1,2,4-triazol-1-yl)-2-hexine and 400 ml of absolute dichloromethane. After the end of the addition, stirring is continued for one hour at 0° C. The reaction mixture is then subjected twice to extraction by shaking with saturated aqueous sodium carbonate solution. The organic phase is dried over sodium sulphate and concentrated under reduced pressure. This gives 76.3 g of a product which consists to the extent of 70.5% of 5-(1-chlorocyclopropyl)-2,3-dibromo-5-hydroxy-6-( 1,2,4-triazol-1-yl)-2-hexene. For purification, the product is chromatographed on silica gel using ethyl acetate. 5-(1-Chlorocyclopropyl)-2,3-dibromo-5-hydroxy-6-(1,2,4-triazol-1-yl)-2-hexene is thus obtained in the form of a solid of melting point 55°–56° C.

$^1$H-NMR (200 MHz, CDCl$_3$): δ=0.4 (m, 2H); 0.8 (m, 1H); 1.05 (m, 1H); 2.5 (s, 3H); 3.1 (d, 1H); 3.7 (d, 1H); 4.15 (OH); 4.45 (d, 1H); 8.0 (s, 1H); 8.3 (s, 1H) ppm.

Example 2

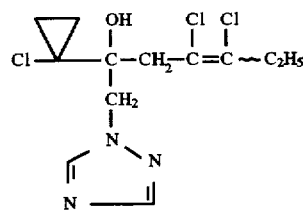
(I-2)

1st stage

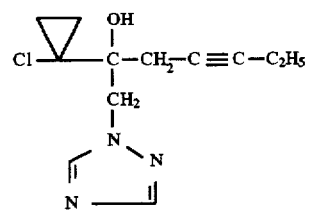
(VI-2)

89.7 ml (021 mol) of n-butyllithium in hexane are added at −40° C., with stirring and under a nitrogen atmosphere, to a solution of 22.5 g (0.1 mol) of 4-(1-chlorocyclopropyl) 4hydroxy-5-(1,2,4-triazol-1-yl)1-pentine in 350 ml of liquid ammonia. After the end of the addition, stirring is continued initially at from −30° C. to −40° C. for 1 hour, and then a solution of 17.2 g (0.11 mol) of ethyl iodide in 20 ml of absolute tetrahydrofuran is added dropwise. The reaction mixture is subsequently stirred under ammonia reflux. For working up, the ammonia is evaporated off, ethyl acetate and water are added to the residue, and the organic phase is separated off, dried over sodium sulphate and concentrated under reduced pressure. This gives 25 g of a product which consists to the extent of 85.3% of 6-(1-chlorocyclopropyl)-6-hydroxy-7-(1,2,4-triazol-1-yl)-3-heptine. Recrystallization from ethanol gives 6-(1-chlorocyclopropyl)-6-hydroxy-7-(1,2,4triazol-1-yl)3-heptine in the form of a solid of melting point 83°–84° C.

2nd stage

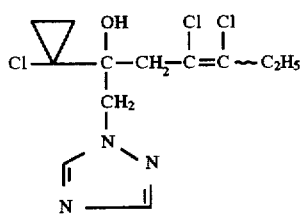
(I-2)

26.1 g (0.368 mol) of chlorine gas are passed at from 0° C. to 5° C. and with stirring over the course of 4 hours into a solution of 71.9 g (0.284 mol) of 6-(1-chlorocyclopropyl) 6-hydroxy-7-(1,2,4-triazol-1-yl)-3-heptine in 1.1 liters of dichloromethane. The reaction mixture is then diluted with dichloromethane and subjected several times to extraction by shaking with saturated aqueous sodium carbonate solution. The organic phase is dried over sodium sulphate and concentrated under reduced pressure. The residue comprises 96.1 g of a product which consists to the extent of 77.5% of 6-(1-chlorocyclopropyl)-3,4-dichloro-6-hydroxy-7-(1,2,4-triazol-1-yl)-3-heptene. Recrystallization from ethanol gives 6-(1-Chlorocyclopropyl)-3,4-dichloro-6hydroxy-7-(1,2,4-triazol-1-yl)-2-heptene in the form of a solid of melting point 79°–80° C.

$^1$H-NMR (200 MHz, CDCl$_3$): δ=0.4 (m, 2H); 0.85 (m, 1H); 1.05 (m, 1H); 1.15 (t, 3H); 2.65 (q, 2H); 2.95 (d, 1H); 3.45 (d, 1H); 4.15 (OH); 4.35 (d, 1H); 4.95 (d, 1H); 8.0 (s, 1H); 8.3 (s, 1H) ppm.

Example 3

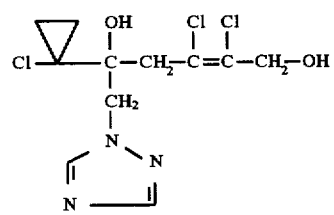
(I-3)

1st stage

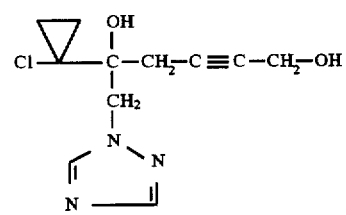
(VI-3)

9.4 ml (22 mmol) of n-butyllithium in hexane are added at −20° C., with stirring and under a nitrogen atmosphere, to a solution of 2.25 g (10 mmol) of 4-(1-chlorocyclopropyl) 4-hydroxy-5-(1,2,4triazol-1-yl)-1-pentine in 40 ml of absolute tetrahydrofuran. After the end of the addition, stirring is initially continued at 0° C. for 30 minutes. Then 0.6 g (20 mmol) of gaseous formaldehyde, which has been prepared by depolymerization of 0.6 g of paraformaldehyde at 150° C., is passed in in a stream of nitrogen. The reaction mixture is then stirred at 0° C. for 2 hours more before being diluted with ethyl acetate and subjected several times to extraction by shaking with saturated aqueous ammonium chloride solution. After the organic phase has been dried over sodium sulphate, it is concentrated by stripping off the solvent under reduced pressure. This gives 2.2 g (86% of theory) of 5-(1-chlorocyclopropyl)-1,5-dihydroxy-6-(1,2,4-triazol-1-yl)-2-hexine in the form of an oil.

$^1$H-NMR (200/MHz, CDCl$_3$, TMS). δ=0.5–1.2 (m, 4H); 2.8 (m, 2H); 4.25 (m, 2H); 4.5 (OH); 4.65 (AB, 2H); 8.0 (s, 1H); 8.3 (s, 1H) ppm.

2nd stage

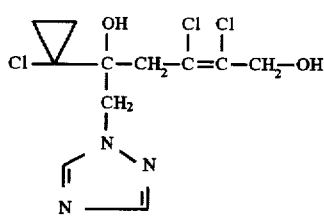

(I-3)

A stream of chlorine gas is passed at 0° C. with stirring for two hours into a solution of 2.5 g (10 mmol) of 5-(1-chlorocyclopropyl)-1,5-dihydroxy-6-(1,2,4-triazol-1-yl)-2-hexine in 30 ml of absolute dichloromethane. The reaction mixture is then diluted with dichloromethane and subjected several times to extraction by shaking with saturated aqueous sodium carbonate solution. The organic phase is dried over sodium sulphate and concentrated under reduced pressure. The residue comprises 3.4 g of a product which is chromatographed over 300 g of silica gel using ethyl acetate. This gives 1.3 g (40% of theory) of 5-(1-chlorocyclopropyl)-2,3-dichloro-1,5-dihydroxy-6-(1,2,4-triazol-1-yl)-2-hexene in the form of a solid of melting point 130°–132° C.

Example 4

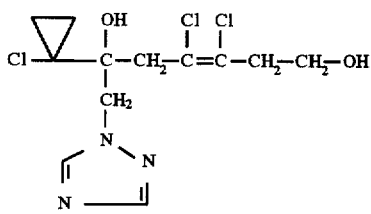

(I-4)

1st stage

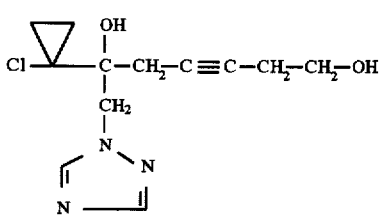

(VI-4)

9.4 ml (22 mmol) of n-butyllithium in hexane are added at –20° C., with stirring and under a nitrogen atmosphere, to a solution of 2.25 g (10 mmol) of 4-(1-chlorocyclopropyl)-4-hydroxy-5-(1,2,4-triazol-1-yl)-1-pentine in 30 ml of absolute tetrahydrofuran. After the end of the addition, stirring is initially continued at 0° C. for 30 minutes. Then 0.74 ml (15 mmol) of ethylene oxide and 1.6 g (15 mmol) of lithium perchlorate are added at 0° C. with stirring. After the end of the addition, stirring is continued at room temperature for 24 hours, then the mixture is diluted with ethyl acetate and is subjected several times to extraction by shaking with saturated aqueous ammonium chloride solution. After the organic phase has been dried over sodium sulphate, it is concentrated by stripping off the solvent under reduced pressure. This gives 2.7 g of a product which consists to the extent of 72% of 6-(1-chlorocyclopropyl)-1,6-dihydroxy-7-(1,2,4triazol-1-yl)-3-heptine.

GC/MS (CI): 270 (M+H$^+$,100%, 1 Cl).

2nd stage

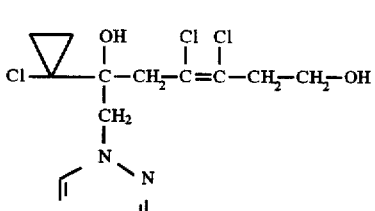

(I-4)

A stream of chlorine gas is passed at from 0° C. to 5° C. with stirring for two hours into a solution of 2.7 g (10 mmol) of 6-(1-chlorocyclopropyl)-1,6-dihydroxy-7-(1,2,4-triazol-1-yl)-3-heptine in 30 ml of absolute dichloromethane. The reaction mixture is then diluted with dichloromethane and subjected several times to extraction by shaking with saturated aqueous sodium carbonate solution. The organic phase is dried over sodium sulphate and concentrated under reduced pressure. The residue comprises 2.88 g of a product which is chromatographed over 200 g of silica gel using ethyl acetate. This gives 0.8 g (24% of theory) of 6-(1-chlorocyclopropyl)-3,4-dichloro-1,6-dihydroxy-7-(1,2,4-triazol-1-yl)-3-heptene.

GC/MB (CI): 340 (M+H$^+$, 100%, 3 Cl).

The substances according to the invention which are listed in the table below are also prepared by the methods described above.

TABLE 2

| | | | | | | |
|---|---|---|---|---|---|---|
| Ex. No. | Compd. No. | $R^1$ | $X^1$ | $X^2$ | Y | $R^2$ | Melting point °C. |
| 5 | I-5 | Cl-△ | Cl | Cl | N | —CH$_3$ | oil |
| 6 | I-6 | Cl-△ | Cl | Cl | CH | —CH$_3$ | 149–152 |

(I) structure: $R^1$—C(OH)—CH$_2$—C($X^1$)=C($X^2$)—$R^2$ with CH$_2$-triazolyl(Y) substituent TABLE 2-continued $$R^1-\underset{\underset{\underset{\underset{N\diagdown}{\overset{|}{N}}}{\overset{|}{CH_2}}}{\overset{|}{CH_2}}}{\overset{\overset{OH}{|}}{C}}-CH_2-\overset{\overset{X^1}{|}}{C}=\overset{\overset{X^2}{|}}{C}-R^2 \quad (I)$$

| Ex. No. | Compd. No. | R¹ | X¹ | X² | Y | R² | Melting point °C. |
|---|---|---|---|---|---|---|---|
| 7 | I-6 | 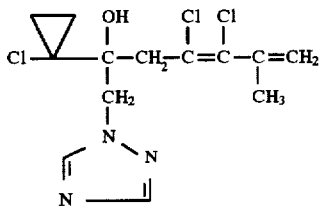 | Cl | Cl | N | —C₄H₉-n | 72–74 |
| 8 | I-8 |  | Br | Br | N | —C₂H₅ | 75–77 |
| 9 | I-9 |  | Br | Br | N | —C₄H₉-n | oil |
| 10 | I-10 |  | Cl | Cl | N | —CH—CCl₃<br>   \|<br>  OH | oil |
| 11 | I-11 |  | Br | Br | N | —CH₂—OH | 135–136 |
| 12 | I-12 |  | Br | Br | N | —CH—CH₃<br>  \|<br> OH | oil |
| 13 | I-13 |  | Cl | Cl | N | CH₃<br>\|<br>—C—CH₃<br>\|<br>OH | oil |

Example 14

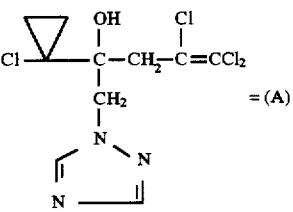

(I-14)

0.71 g (6 mmol) of thionyl chloride are added at room temperature with stirring to a mixture of 1.77 g (5 mmol) of 6-(1-chlorocyclopropyl)-3,4-dichloro-2,6-dihydroxy-2-methyl-7-(1,2,4-triazol-1-yl)-hept-3-ene and 20 ml of methylene chloride, and the mixture is then heated at reflux for 5 hours. Aqueous sodium carbonate solution is subsequently added to the reaction mixture, which is then subjected several times to extraction with methylene chloride. The combined organic phases are dried over sodium sulphate and concentrated under reduced pressure. The product which remains is chromatographed over silica gel using ethyl acetate. Concentration of the eluate gives 0.5 g (20% of theory) of 6(1-chlorocyclopropyl)-3,4dichloro-6-hydroxy-2-methyl-7-(1,2,4-triazol-1-yl)hepta-1,3-diene in the form of a colourless oil.

In the use examples which follow, the compound of the formula indicated below is employed as comparison substance:

$$Cl-\underset{}{\triangledown}-\underset{\underset{\underset{\underset{N\diagdown}{\overset{|}{N}}}{\overset{|}{CH_2}}}{\overset{|}{CH_2}}}{\overset{\overset{OH}{|}}{C}}-CH_2-\overset{\overset{Cl}{|}}{C}=CCl_2 \quad =(A)$$

(known from EP-A 0 440 949)

Example A

Botrytis test (bean)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, each leaf is provided with 2 small agar pieces on which Botrytis cinerea is growing. The inoculated plants are placed in a darkened, humid cabin at 20° C. Evaluation is carried out, 3 days after the inoculation, of the size of the disease spots on the leaves.

Active compounds, active-compound concentrations and test results are shown in the following table.

TABLE A

Botrytis test (bean)/protective

| Active compound | Degree of action as % of the untreated control at an active-compound concentration of 100 ppm |
|---|---|

According to the invention:

Cl—[cyclopropyl]—C(OH)(CH₂-triazolyl)—CH₂—CBr=CBr—C₂H₅  (I-8)   99

$$Cl-\triangle-\underset{\underset{\underset{N\diagdown N}{\underset{\|}{N-\!-\!\!-\!\!-\!\!\|}}}{\underset{|}{CH_2}}}{\overset{OH}{\underset{|}{C}}}-CH_2-\overset{Br}{\underset{|}{C}}=\overset{Br}{\underset{|}{C}}-C_2H_5$$

Example B

*Leptosphaeria nodorum* test (wheat)/curative
Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are sprayed with a spore suspension of *Leptosphaeria nodorum*. The plants remain for 48 hours in an incubation cabin at 20° C. and 100% relative atmospheric humidity. The plants are then sprayed with the active compound preparation at the application rate indicated.

The plants are placed in a greenhouse at a temperature of about 15° C. and a relative atmospheric humidity of about 80%.

Evaluation is carried out 10 days after the inoculation.

Active compounds, active-compound concentrations and test results are shown in the following table.

TABLE B

*Leptosphaeria nodorum* test (wheat)/curative

| Active compound | | Degree of action as % of the untreated control at an active-compound application rate of 125 g/ha |
|---|---|---|

Known from EP-A 0 440 949:

$$Cl-\triangle-\overset{OH}{\underset{|}{C}}(CH_2\text{-triazolyl})-CH_2-\overset{Cl}{\underset{|}{C}}=CCl_2 \quad (A) \quad 37$$

According to the invention:

$$Cl-\triangle-\overset{OH}{\underset{|}{C}}(CH_2\text{-triazolyl})-CH_2-\overset{Br}{\underset{|}{C}}=\overset{Br}{\underset{|}{C}}-C_2H_5 \quad (I\text{-}8) \quad 83$$

Example C

*Pyrenophora teres* test (barley)/protective
Solvent: 10 parts by weight of N-methyl-pyrrolidone
Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate indicated.

After the spray coating has dried on, the plants are sprayed with a conidia suspension of *Pyrenophora teres*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

Active compounds, active-compound concentrations and test results are shown in the following table.

TABLE C

*Pyrenophora teres* test (barley)/protective

| Active compound | Degree of action as % of the untreated control at an active-compound application rate of 125 g/ha |
|---|---|
| Known from EP-A 0 440 949: 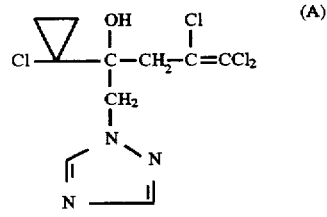 (A) | 89 |
| According to the invention: 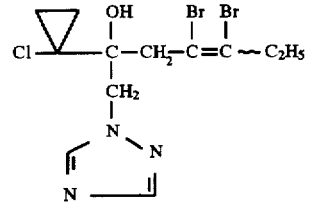 (I-8) | 100 |

Example D

Materials protection test

For demonstrating the activity against fungi, the minimum inhibitory concentrations (MIC values) of compounds according to the invention are determined:

An agar prepared using malt extract is treated with active compounds according to the invention in concentrations of from 0.1 mg/l to 800 mg/l. Following solidification of the agar, it is contaminated with pure cultures of respective microorganisms. After storage for two weeks at 28° C. and a relative atmospheric humidity of from 60 to 700%, the minimum inhibitory concentration (MC value) is determined. The MIC value denotes the lowest concentration of active substance at which there is no infestation by the species of microbe used.

Active compounds, active-compound concentrations and test results are shown in the following table.

TABLE D

Materials protection test

| Microorganism | Minimum inhibitory concentration (MIC value) in mg/l for the active compounds | | |
|---|---|---|---|
| | (I-2) | (I-8) | (A) |
| *Penicillium brevicaule* | <50 | 5 | 75 |
| *Chaetomium globosum* | <50 | 5 | <50 |
| *Aspergillus niger* | <50 | 1 | 3 |
| *Sclerophoma pityophila* | 5 | <1 | <1 |

TABLE D-continued

Materials protection test

| Microorganism | Minimum inhibitory concentration (MIC value) in mg/l for the active compounds | | |
|---|---|---|---|
| | (I-2) | (I-8) | (A) |
| *Trichoderma viride* | 20 | 20 | 35 |
| *Cladosporium herbarum* | 5 | 5 | <1 |
| *Alternaria tenuis* | 5 | 5 | 35 |
| *Aureobasidium pullulans* | 1 | 1 | 5 |

Example E

Coatings test

The compound (I-8) to be tested for its fungicidal activity was incorporated in various concentrations in a polyvinyl acetate emulsion paint. The paint was then brushed onto both sides of an appropriate substrate. Some of the test specimens were washed out with running water (24 h; 20° C.) before the test for mould resistance.

The test specimens prepared in this way were placed on an agar culture medium. Test specimens and culture medium were contaminated with fungal spores of the paint-destroying fungi *Alternaria tenuis, Aspergillus flavus, Aspergillus ustus, Aspergillus niger, Cladosporium herbarum, Paecilomyces variotii, Penicillium citrinum, Aureobasidium pullulans* and *Stachybotrys atra Corda*. Evaluation was made after storage for 3 weeks at 29°±1° C. and a relative atmospheric humidity of from 80 to 90%.

Paint films with the compound (I-8) according to the invention but which had not been washed out exhibit good mould resistance from an active-compound content of 0.3%; in those specimens which had been washed out, a good activity was observed at an active-compound content of 0.6%.

Example F
Wood test

Sections of mycelium were punched out from colonies of wood-destroying Basidiomycetes and were incubated on an agar culture medium at 26° C. The inhibition of hyphal growth on culture media containing active compound was compared with that on nutrient media without the addition of active compound, and was rated as the percentage inhibition.

A 100% activity was achieved by the compound (I-8) according to the invention against the brown rot causative organisms *Gloeophyllum trabeum* and *Poria placenta* and against the white rot causative organism *Lentinus tigrinus* at just 1 ppm.

We claim:

1. A halogenoalkenyl-azolyl derivative of the formula

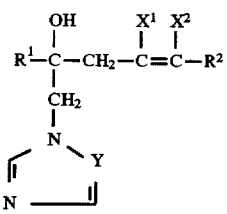

in which

R$^1$ represents cycloalkyl having 3 to 7 carbon atoms, or represents monosubstituted to trisubstituted cycloalkyl with 3 to 7 carbon atoms, the substituents being selected from halogen and alkyl having 1 to 4 carbon atoms, R$^2$ represents straight-chain or branched alkyl having 1 to 6 carbon atoms, straight-chain or branched halogenoalkyl having 1 to 6 carbon atoms and 1 to 5 fluorine atoms or chlorine atoms, or represents straight-chain or branched 1-hydroxyalkyl having 1 to 6 carbon atoms, or represents straight-chain or branched 2-hydroxyalkyl having 2 to 6 carbon atoms, straight-chain or branched 1-hydroxyhalogenoalkyl having 1 to 6 carbon atoms and 1 to 3 halogen atoms, straight-chain or branched 1-alkenyl having 2 to 6 carbon atoms, or represents straight-chain or branched 2-alkenyl having 2 to 6 carbon atoms, X$^1$ represents fluorine, chlorine, bromine or iodine, and X$^2$ represents fluorine, chlorine, bromine or iodine, or an addition product thereof with an acid or metal salt.

2. A halogeno-alkenyl-azolyl derivative according to claim 1 wherein

R$^1$ represents a cyclopropyl group which is optionally monosubstituted to trisubstituted by halogen or C$_1$–C$_4$-alkyl, and R$^2$ represents straight-chain or branched alkyl having 1 to 6 carbon atoms, straight-chain or branched halogenoalkyl having 1 to 6 carbon atoms and 1 to 5 fluorine atoms or chlorine atoms, or represents straight-chain or branched 1-hydroxyalkyl having 1 to 6 carbon atoms, or represents straight-chain or branched 2-hydroxyalkyl having 2 to 6 carbon atoms, or straight-chain or branched 1-hydroxyhalogenoalkyl having 1 to 6 carbon atoms and 1 to 3 halogen atoms.

3. A halogenoalkenyl-azolyl derivative according to claim 1, wherein

R$^1$ represents 1-methyl-cyclohexyl, cyclohexyl, 1-chloro-cyclopropyl, 1-methylcyclopropyl, cyclopropyl, 1-methylcyclopentyl, cyclopentyl or 1-ethylcyclopentyl, R$^2$ represents methyl, ethyl, n-propyl, i-butyl, n-butyl, n-pentyl, chloromethyl, fluoromethyl, 2-chloroethyl, 2-fluoroethyl, 3-chloropropyl, 3-fluoropropyl, trichloromethyl, trifluoromethyl, hydroxymethyl, 1-hydroxyethyl, 1-hydroxy-propyl, 1-hydroxy-butyl, 2-hydroxy-prop-2-yl, 3-hydroxy-but-2-yl, 3-hydroxy-pent-3-yl, 2-hydroxy-ethyl, 2-hydroxy-1-propyl, 2-hydroxy-2-methyl-propyl, 2-hydroxy-1-butyl, 1-hydroxy-2,2,2-trichloroethyl, vinyl, 1-propenyl, 1-butenyl, 2-butenyl, 1-propen-2-yl or 2-buten-2-yl, X$^1$ represents fluorine, chlorine, bromine or iodine and X$^2$ represents fluorine, chlorine, bromine or iodine.

4. A halogeno-alkenyl-azolyl derivative according to claim 2, wherein R$^1$ represents a 1-chloro-cyclopropyl group.

5. The halogenoalkenyl-azolyl derivative according to claim 1 which is

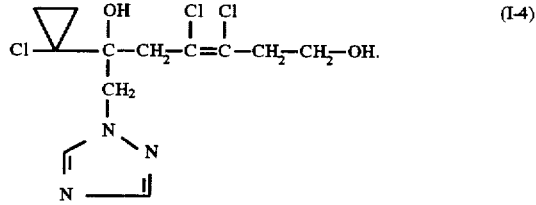

6. The halogenoalkenyl-azolyl derivative according to claim 1, which is

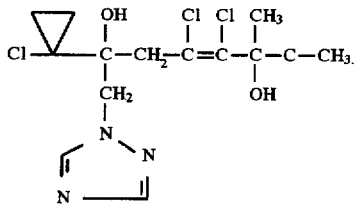

7. The halogenoalkenyl-azolyl derivative according to claim 1, which is

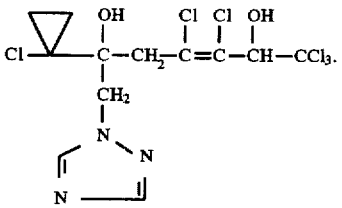

8. The halogenoalkenyl-azolyl derivative according to claim 1 which is

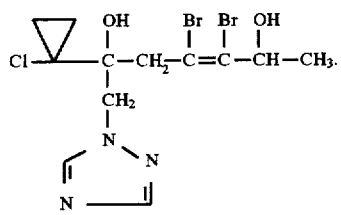

9. The halogenoalkenyl-azolyl derivative according to claim 1, which is

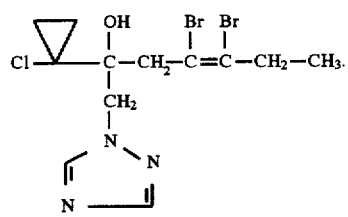

10. The halogenoalkenyl-azolyl derivative according to claim 1, which is

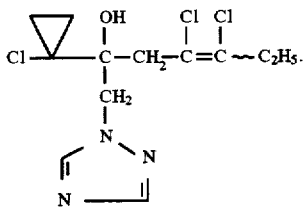

11. A microbicidal composition which comprises a microbicidally effective amount of a compound according to claim 1 or an addition product thereof with an acid or metal salt and an inert diluent.

12. A method for combating unwanted microorganisms in plants or for protecting materials from unwanted microorganisms, which comprises applying a microbicidally effective amount of a compound according to claim 11 or an addition product thereof with an acid or a metal salt to the microorganism or to the material or to a habitat where the microorganism resides.

* * * * *